United States Patent [19]

Meyer et al.

[11] Patent Number: 5,958,340
[45] Date of Patent: Sep. 28, 1999

[54] SOLID-STATE CHEMICAL SENSOR

[75] Inventors: Joerg-Uwe Meyer, Ingbert; Andrea Haeusler, Hamburg, both of Germany

[73] Assignee: Fraunhofer-Gesellschaft zur Foerderung der angewandten Forschung e.V., Munich, Germany

[21] Appl. No.: 09/091,000

[22] Filed: Jun. 5, 1998

Related U.S. Application Data

[63] Continuation of application No. 08/840,838, Apr. 17, 1997, abandoned, which is a continuation of application No. PCT/EP95/04108, Oct. 19, 1995.

[30] Foreign Application Priority Data

Oct. 21, 1994 [DE] Germany ............................. 44 37 692

[51] Int. Cl.⁶ .................................................. G01N 27/04
[52] U.S. Cl. ................................. 422/90; 422/94; 422/98; 205/783.5; 205/784; 205/784.5; 257/204; 257/253; 324/439; 324/443; 73/31.06
[58] Field of Search ........................ 204/415; 422/82.02, 422/94, 98, 83, 90; 257/43, 204, 205, 253, 288; 324/439, 443; 73/31.06; 205/783.5, 784, 784.5

[56] References Cited

U.S. PATENT DOCUMENTS

| | | | |
|---|---|---|---|
| 4,045,178 | 8/1977 | Okinaka et al. | 422/98 |
| 4,885,929 | 12/1989 | Kasahara et al. | 422/98 |
| 5,457,333 | 10/1995 | Fukui | 257/253 |
| 5,618,496 | 4/1997 | Hasumi et al. | 422/98 |

FOREIGN PATENT DOCUMENTS

| | | |
|---|---|---|
| 0 488 503 | 6/1992 | European Pat. Off. . |
| 51-42180 | 6/1993 | Japan . |

OTHER PUBLICATIONS

Yan, Beiping et al., "Gas–sensing properties of alfa–Fe2O3 thin films prepared by plasma–enhanced chemical vapour deposition", Thin Solid Films, 245, 1994, pp. 225–227. No month available.

*Primary Examiner*—Bruce F. Bell
*Attorney, Agent, or Firm*—Evenson, McKeown, Edwards & Lenahan P.L.L.C.

[57] ABSTRACT

The invention pertains to a solid-state chemical sensor with a substrate support. On one side of the support is mounted a heating element with branch circuit connections. On the other side interdigital electrodes are arranged and thereon a carbon dioxide-sensitive material, which comprises CuO and $TiO_3$, as well as additional metal oxides, in the form of a thick film of approximately 20–200 $\mu m$.

15 Claims, 3 Drawing Sheets

1)

2)

3)

4)

SOLID-STATE CHEMICAL SENSOR

This application claims the priority of German application number 44 37 692.8 filed on Oct. 21, 1994, the disclosure of which is expressly incorporated by reference herein. This application is a continuation of application Ser. No. 08/840,838, filed Apr. 17, 1997, now abandoned, which application is a continuation of application PCT/EP 95/04108, filed Oct. 19, 1995.

BACKGROUND AND SUMMARY OF THE INVENTION

The present invention relates to an apparatus and method for detecting chemicals.

In industrial and biological processes, the importance of detecting and controlling carbon dioxide ($CO_2$) concentrations continues to grow. The role of $CO_2$ as a pollutant did not receive the attention it deserved until recently with the increasing discussion concerning the so-called "green house effect".

Some semiconductive, solid-state chemicals sensors have been discussed in the art, Technisches Messen, tm 56 (1989) Oldenbourg-Verlag, pp 260–63. These chemical sensors may be applied to industrial and biological applications. In addition, other fields where solid-state chemical sensors may be applied include:

monitoring ventilation and control of air conditioning and ventilation systems;

monitoring air conditioning in green houses and other fields of agriculture;

controlling biological and chemical processes in biotechnology;

monitoring patients; and continuous and comprehensive emission control in industrial combustion processes.

Stricter regulations and growing public awareness with regard to the environment allow one to expect a rising demand for inexpensive $CO_2$ sensors. In addition, concerns about chemical sensors utilized for the detection of carbon dioxide include alterations to the sensor material due to the influence of the gas to be detected. Thus, there is a need in the art for improved $CO_2$ sensors.

Solid Electrolytic Sensors

A solid electrolytic carbon dioxide detecting sensor was developed by T. Maruyama and coworkers (Tokyo Institute of Technology, Japan). It is based on the $Na^+$ ion conductor NASICON. Applied to it is a carbonate electrode, which reacts to changes in $CO_2$ (1–3). When carbon dioxide is introduced, sodium ions form at the anode, which migrate through the carbonate to the electrolyte and reach the cathode. The resulting electromotive power (EMK) can be measured and the $CO_2$ concentration in the sample is determined using the Nernst equation. Some of the major drawbacks of these sensors are the long response times, due to the fact that the rate of change in EMK depends on the diffusion rate of the ions, and that moisture influences the measured results. Another disadvantage is the need for a reference electrode since gas tight measurements are required. To date, it has not been possible to remedy the difficulties involved with a stable reference electrode.

Optical $CO_2$ Sensors

Optical $CO_2$ sensors have also been discussed. For example, a commonly used method for measuring $CO_2$ is infrared absorption. This non-destructive method is based on the capability of $CO_2$ molecules to absorb infrared radiation at specific wave lengths. The method, employing spectrometers, demonstrates stability and accuracy. Nevertheless, such methods and devices are very expensive and usually require complicated equipment. Due to the cost, this method of analysis can be ruled out for general monitoring in the field.

In other optical $CO_2$ sensors, the change in the refractive index measured is a function of the $CO_2$ concentration. At the Fraunhofer Institut für Physikalische Meβtechnik, in Freiburg, Germany an integrated optical sensor in which organically modified silicates are applied as a sensitive film onto an integrated optical interferometer (4), were developed under R. Edelhäuser. The $CO_2$ absorbed on this film caused its refractive index to change. However, the problems of selectivity, time constants, and reversibility can not, to date, be solved.

Another optical measuring method uses a suited indicator, which changes color under the influence of $CO_2$. The intensity of this change in color depends on the gas concentration and is evaluated optically. In this case, an integrated solution is under development (C. H. Morgan, Microsensor Research Laboratory, University of Washington, USA (5) and not ready for general use.

Mass Sensitive Sensors

Gravimetric sensors absorb the gas to be measured on their surface reversibly. The settling of the substance to be examined on the surface of the sensor results in a change in mass and, consequently, in a change in the propagation velocity of the waves and a shift in the resonance frequency. At the Universität Tübingen, Prof. W. Göpel's group coated a quartz microbalance sensor with a silicon based polymer in order to detect carbon dioxide (6). In Nieuwenhuizen et al., poly(ethyleneimine) was applied as a chemical interface for $CO_2$ to a surface acoustic wave sensor (7). However, the sensor proved useless for measuring $CO_2$ due to its great cross sensitivity to water and oxygen. At the same time, sensitivity to $CO_2$ decreased with increasing use and an obvious baseline drift was observed. The characteristic frequency in this group of sensors is distinctly sensitive to temperature as well as to pressure. Thus, at the present state of development, such types of sensors are less suited for $CO_2$ detection.

Ultrasonic Sensor

In this type of sensor, which was developed by V. M. Mecea (Institute of Isotopic and Molecular Technology, Cluj Napoca, Romania), a quartz crystal resonator generates ultrasonic waves in a cavity, which are reflected at the walls of the cavity. If the distance between the quartz surface and the parallel, reflecting walls is an integral multiplicity of the half wavelength, resonance occurs with the gas that is in the cavity and the entire oscillation energy of the resonator is absorbed by the gas. The resonance of $CO_2$ can be obtained by setting the gap a specific length. If there is a small proportion of another gas in the gas flow, the resonance conditions change and this can be evaluated as a signal (8). The disadvantages of this sensor are the great drift in temperature and the lack of selectivity.

Capacitive Measuring Method

In these methods, the dielectric constant of the sensor material changes in that the molecules with a suitable dipole moment are absorbed at the surface of the sensor. However, $CO_2$ does not have a dipole moment. Therefore, materials on which carbon dioxide can be chemisorbed are used for capacitive type $CO_2$ sensors. As a consequence, the end product changes the dielectric constant. The degree of adsorption and the subsequent magnitude of the change in the dielectric constant depends on the $CO_2$ concentration in the vicinity of the sensor. This change can be determined by means of the capacitor structure.

Under E. Obermeier (TU Berlin), a $CO_2$ sensitive, organically modified silicate-based material was applied to thin film produced interdigitated capacitors. The dynamic properties of the sensors are extremely temperature dependent. At the same time, the sensor shows a great sensitivity to moisture (9, 10).

Research regarding a metal-oxide based capacitive measuring method for determining $CO_2$ concentrations was published by a group connected to T. Isihara at the Oita University (Japan). The fundamental idea behind this sensor is based on the fact that the dielectric constants of the metal oxides principally differ from the constants of the metal carbonates (11–14). A powder composed of a mixture of different metal oxides is compressed to form tablets and centered. The electrodes are produced by applying silver to both sides of the tablet in order to obtain a capacitor structure. Wires inserted into the silver droplets are the contact. A rise in the ambient $CO_2$ concentration leads to an increase in sensor capacity. At the same time, water plays a significant role due to its large dielectric constant. This type of $CO_2$ sensor design proves to be very disadvantageous. In sensors, the use of tablets is impractical because they break easily. Resort to the non-reproducible dripping of silver for producing the electrodes, because of the difficulties in contacting tablets made of compressed powder, complicates matters. Even sputtering methods would not lead to solderable or bondable silver due to the thinness of the layer required.

Many other disadvantages of this method exist. The production of the surface and configuration of the electrodes is imprecise and irreproducible. Consequently, sensor capacity as a function of the electrode surface is also irreproducible. It is as if the chemically active layer would be largely shielded from the surroundings by the electrodes. The ratio of volume to surface of the sensor body is very big and the diffusion path is long. Due to the great distance of 0.6mm between the electrodes as a result of the thickness of the tablet, the sensor has a high impedance. The high setting temperature, of approximately 475°, is also required for $CO_2$ detection and has to be executed using an external heating device. Also, detecting the changes in dielectric properties requires a complicated evaluation circuit. Clearly, sensors in tablet form are not suited for mass production.

Polymer Conductive Sensors

The principle of these sensors is based on a change in conductivity due to gas adsorption and the subsequent surface reaction. A certain selectivity is obtained by the choice of the catalyst (15). Preliminary experiments with polymer conductivity sensors were conducted on the basis of PPA (polyphenylacetylene) (16). To date, it has not been possible to put this sensor principle into practice.

The present invention provides a solid-state chemical sensor in which reference electrodes are obviated. The sensor is substantially cheaper than others and permits the determination of close meshed concentrations of pollutants in industry, at the workplace, or in traffic with sufficient accuracy, but at relatively low cost. Monitoring the $CO_2$ concentration in the environment makes it possible to detect environmental hazards and to initiate pinpoint countermeasures.

The solid-state sensor of the invention comprises, for example, a semiconductive solid-state chemical sensor having a ceramic carrier with a heating element having branched circuit connections disposed on one side, and interdigitated electrodes, on the other side. A gas sensitive material is disposed, using thick film technology, on the electrode side. For a $CO_2$ sensor, the gas sensitive material may comprise, for example, CuO and Ba-TiO$_3$ and additional metal oxides as catalysts and/or adhesion compounds in a sintered form. A film thickness of approximately 20–200 $\mu$m is used and conductivity is measured by means of the resistance dependent upon the change in the $CO_2$ concentration.

In other embodiments, the gas sensitive material has a grain size of less than 5 $\mu$m, and preferably in the nano structure range of 1nm to 400 nm. In addition, catalysts may optionally be added to the gas sensitive material at 0.1 to 10%.

Also, a $Cu_xCe_yO_z$ may be employed as metal oxide in the gas sensitive material, with x, y, and z being in the range of approximately 1–5, with x, y, and z not necessarily being integers.

In other embodiments, the interdigitated electrodes may be made of gold or another precious metal. And the heating electrodes may be made of platinum or palladium.

Other objects, advantages and novel features of the present invention will become apparent from the following detailed description of the invention when considered in conjunction with the accompanying drawings.

DETAILED DESCRIPTION

Figure 1:
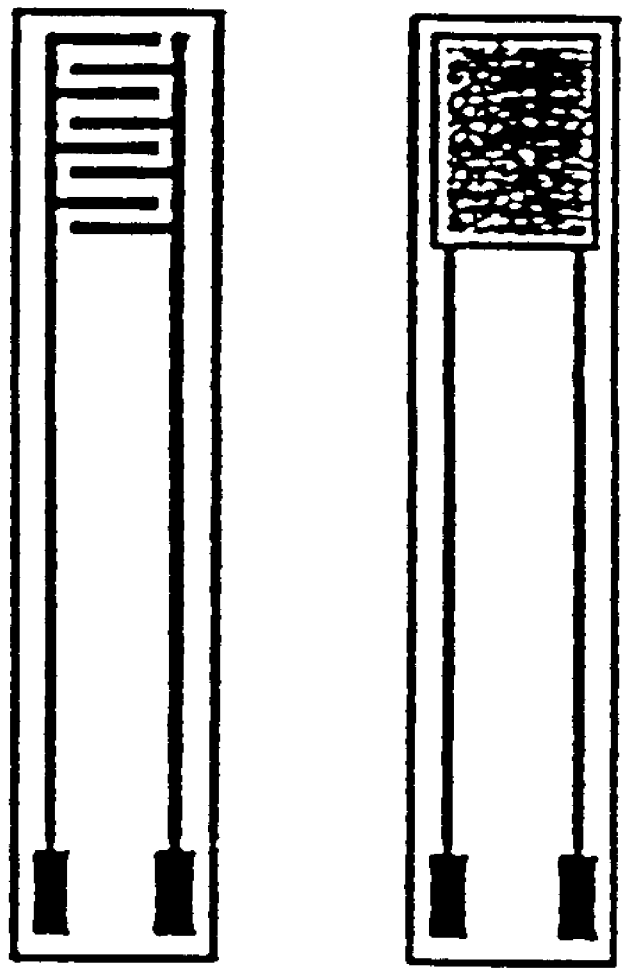
FIG. 1: Diagrammatic view of a $CO_2$ metal oxide conductivity sensor fabricated by means of thick film technology (scale approximately 2:1).

A thick film metal oxide conductivity sensor was developed, which responds to a change in the concentration of carbon dioxide in its vicinity by increasing or decreasing resistance. Due to the way it functions, through a change in conductivity as a consequence of a change in the $CO_2$ concentration, a simple electronic circuit can be employed to evaluate the sensor signal.

As the resistance of the sensor is measured to determine the $CO_2$ concentration, the sensor has a very simple structure and can be fabricated using thick film technology. In this manner, it has been possible to produce $CO_2$ conductivity sensors in a process suited for mass production due to its simplicity, its widespread industrial accessibility, its minimal use of equipment, its low cost, and its efficiency.

The selection of the starting materials involves considering not only a good response to the changes in the $CO_2$ concentration but also a good adhesion of the gas sensitive material to the ceramic. In producing the sensors of the invention, the glass frit customarily employed in thick film technology may be omitted.

With its large measuring range (up to 25 vol% $CO_2$), the sensor is suited for a wide field of applications.

A metal oxide conductivity sensor for the detection of carbon dioxide was developed. The sensor reacts reversibly with a change in resistance to a change in the proportion of $CO_2$ in the ambient atmosphere. This sensor can be utilized in a large measuring range for determining the concentration of $CO_2$.

In the $CO_2$ metal oxide conductivity sensor, sensor resistance is evaluated as the function of the $CO_2$ concentration, thereby permitting setting up the sensor as a simple structure. Two interdigitated structures are employed as electrodes onto which the sensor material is applied.

Due to the materials selected for the sensor and the sensor's simple structure, the advantages of thick film technology can be exploited for fabricating the sensors. Reproducible sensors can be fabricated using thick film technology. The electrodes and the sensor surface may be printed using screen printing, for example. Thus, efficient fabrication of the sensor is ensured.

The heating structure, which is required for obtaining the necessary operating temperature, is printed onto the bottom side of the sensor body. Good thermal transmission is achieved by coupling the heating structure directly to the substrate and consequently less energy is required to operate the sensor. As the temperature at the connecting pads is only approximately 150° C. during operation, despite a sensor temperature of up to 650° C., contacting by means of soldering, bonding or clamping can be easily realized.

The selection of the configuration of the electrodes, two interdigitated structures, which are printed directly onto the substrate, permits applying the active film in the last step of the printing process and in this way it is not covered by any other layer. This means that the entire surface of the metal oxide material may act as the active film.

The use of a glass frit, usually employed for adhesion purposes in thick film technology, is obviated by the selection of the substance for the active sensor film according to the invention. The sensor material adheres well and at the same time possesses great porosity. Due to the relative thin nature of the film, a favorable ratio of sensor volume to sensor surface is obtained. As the effects predominantly occur at the grain boundaries, the sensitivity of the sensor is increased and the response time is decreased. In addition, the simple sensor structure permits a minimizing of the internal resistance of the sensor.

Since the principle underlying the sensor of the invention is based on a change in the conductivity of the gas sensitive material as a consequence of raising or reducing the concentration of the defect electrons due to chemisorption of $CO_2$ on the surface of the sensor, only a simple, inexpensive measuring method is needed to determine the $CO_2$ concentration. Evaluation of a resistance change can be realized in a substantially simpler and uncomplicated manner than, for example, a capacitive sensor.

In addition, the high operating temperature of approximately 570° C. reduces cross sensitivity to water. Also, the ability to combine several different sensors on a small sized substrate to a sensor matrix permits compensating interferences.

The best prerequisites for mass production of the $CO_2$ metal oxide conductivity sensor are given with good reproducibility, low investment costs, efficiency, versatile sensor design, ability to miniaturize, simple fabrication of passes according to laboratory standards, and simplicity of the process. Since the production costs per $CO_2$ sensor are very low, widespread availability is feasible.

One embodiment of the invention, employing the metal oxide conductivity sensor, is shown in FIG. 1. A front and back view is shown. The basic sensor body is composed of aluminum oxide ceramic. Two interdigitated electrodes made of gold are printed onto its front side. A heating structure printed on the bottom side of the ceramic permits setting the required operating temperature.

CuO and $BaTiO_3$ are employed as the starting materials for making the $CO_2$ sensitive metal oxide paste used as the gas sensitive material. Grains of both materials are first ground separately in a planetary mill to obtain grain sizes of less than 5 $\mu$m. Following the grinding procedure, these substances are mixed in a specific ratio with additional metal oxides, which serve as catalysts and adhesion compounds.

Generally in thick film techniques, the addition of organic binders, organic solvents, and a glass frit is necessary to obtain a thick film paste. However, glass frits seal the surface of the sensor tightly. But determining the $CO_2$ concentration may require the disposal of as large as possible a sample of the surface. Therefore, a glass frit was not used, and adhesion of the sensor materials on the $Al_2O_3$ ceramic was ensured by means of the choice of metal oxides.

Various metal oxides may be used as additional metal oxides, for example, $La_2O_3$, $ZrO_2$, and $V_2O_5$. A preferred embodiment employs a mixture of $Cu_xCe_yO_z$, with Cu and $CeO_2$ being sputtered onto the substrate in the presence of oxygen and the coating being finely ground. The x,y,z in the above formula are in the range of about 1–5 and are not necessarily integers.

The paste mixture is put in a planetary mill in order to obtain a homogeneous mixture of the substances. The finished paste is applied onto the interdigitated structure by, for example, a means of screen printing. During the subsequent drying phase, the volatile organic solvents are eliminated from the paste. Sintering the paste occurs in two steps. First, the organic parts of the paste are burned out. Second, the actual sintering procedure occurs following another rise in temperature.

For completion of the sensor, wires are soldered to the pads, thereby ensuring appropriate contacts. The sensor temperature is set at a specific value.

Experiments were conducted at a computer controlled measuring site. A nitrogen-oxygen mixture with a composition corresponding to artificial air was employed as the scavenging and carrier gas. Various test gases in desired concentrations can be added to this carrier gas. The measuring chamber is first scavenged with artificial air. If the amount of $CO_2$ is raised, the sensor resistance is increased. Reduction of the $CO_2$ concentration lets the sensor resistance drop again.

The oxygen adsorbed at the metal oxide surface acts as a surface acceptor and removes electrons from the valence band, which leads to an increase in the concentration of the charge carriers (defect electrons). As the materials used in the example are a mixture with a large proportion of conducting metal oxides, conductivity is increased. The addition of carbon dioxide in the ambient atmosphere of the sensor leads to reactions between the adsorbed oxygen and the $CO_2$. The result is a decrease in the surface oxygen cover and a loss of electrons to the sensor material. This leads to a reduction in the charge carrier concentration and, consequently, to an increase in the sensor resistance. These surface reactions are, for their part, determined by the concentration dependent and catalyst dependent balance between adsorption and desorption. Therefore, conductivity depends on the $CO_2$ concentration. There is a logarithmic relationship between the change in the $CO_2$ concentration and the change in the resistance of the sensor. One skilled in the art will appreciate other ways in which the invention, as it is described, can be modified to effect the same adsorption and desorption results.

Figure 2:
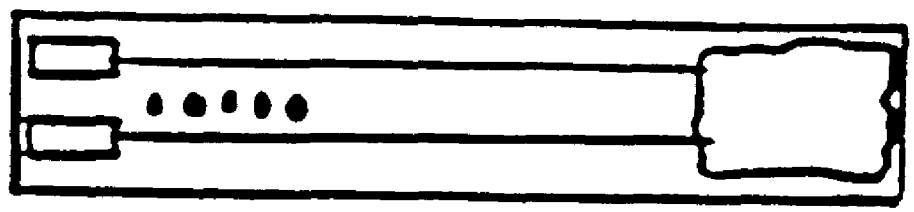
FIG. 2: $CO_2$ metal oxide conductivity sensor fabricated using thick film technology methods.
Figure 2:
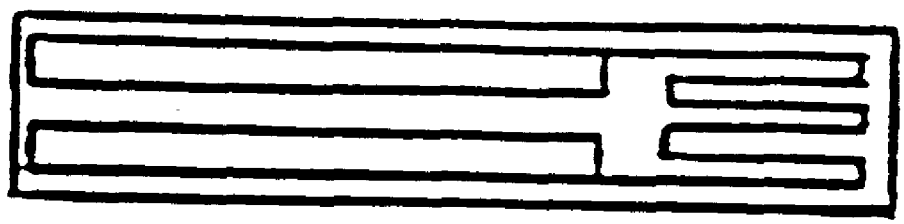
Figure 3:
FIG. 3: Layers of a thick film $CO_2$ sensor in one embodiment.
Figure 3:
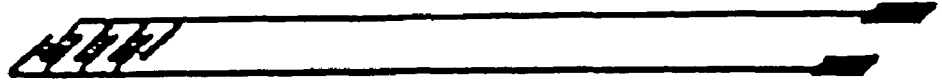
Figure 3:
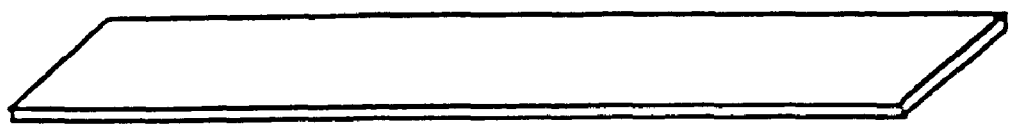
Figure 3:

In a preferred embodiment, a $CO_2$ metal oxide conductivity sensor as shown in FIG. 2 is fabricated using thick film technology methods known in the art. As shown in FIG. 3, an aluminum ceramic substrate (3) is the basic sensor body. On the bottom side is the heating structure (4), with which the required operating temperature of the sensor can be set. The interdigitated electrodes (2), which may be made of gold, are printed onto the top side of the ceramic substrate. These electrodes are covered by the sensor material (1) or gas sensitive material.

After sintering, the thick film made of the sensor material is in the range of 20–200 μm with the material possessing a grain size of 1 nm–400 nm.

Although the invention has been described and illustrated in detail, it is to be clearly understood that the same is by way of illustration and example, and is not to be taken by way of limitation. The spirit and scope of the present invention are to be limited only by the terms of the appended claims.

Each of the following may be relied on to make or use embodiments of the invention. In addition, the entire contents of each of the following references is specifically incorporated herein by reference.

1. Maruyama, T., Sacaki, S., Saito, Y.: Potentiometric Gas Sensor for Carbon Dioxide Using Solid Electrolytes, Solid State Ionics 23:107–112, 1987.
2. Maruyama, T., Ye, X. -Y., Saito, Y.: Electromotive Force of the CO—$Co_2$—$O_2$ Concentration Cell Using $Na_2CO_3$ as a Solid Electrolyte at Low Oxygen Partial Pressure. Solid State Ionics 23:113–117, 1987.
3. Saito, Y., Maruyama, T.,: Recent Developments of the Sensors for Carbon Oxides Using Solid Electrolytes, Solid State Ionics 28–30:1644–1647, 1988.
4. Branderburg, A., Edelhäuser, R., Hutter, F.: Integrated Optical Gas Sensors Using Organically Modified Silicates as Sensitive Films. Sensors and Actuators B 11:361–374, 1993.
5. Morgan., Ch. H., Cheung. P. W.: An Integrated Optoelectronic $CO_2$ Gas Sensor. Digest of Technical Papers, Transducers '91, IEEE 343–346, 1991.
6. Zhou, R., Vaihinger, S., Geckeler, Göpel, W.,: Reliable $CO_2$ Sensors with Silicon-Based Polymers on Quartz Microbalance Transducers. Sensors and Actuators B 18–19:415–420, 1994.
7. Nieuwenhuizen, M. S., Nederlof, A. J.: A SAW Gas Sensor for Carbon Dioxide and Water. Preliminary Experiments. Sensors and Actuators B 2:97–101, 1990.
8. Mecea, V. M.: Tunable Gas Sensors. Sensors and Actuators B 15–16: 265–269, 1993.
9. Lin, J., Heurich, M., Schlichting, V., Obermeier, E.: Characterization and Optimization of a $CO_2$-Sensitive Organically-Modified Silicate with Respect to its Use as a Gas Sensor. Sensors and Actuators B 13–14:528–529, 1993.
10. Heurich, M., Lin, J., Schlichting, V., Obermeier, E.: $CO_2$-Sensitive Organically Modified Silicates for Application in a Gas Sensor. In: Micro-System Technologies 92. Reichl, H. (ed.) Berlin, Offenbach. VDE Verlag GmbH. 1992. pp.359–367.
11. Isihara, T., Kometani, K., Mizuhara, Y., Takita, Y.: Mixed Oxide Capacitor of CuO—$BaSnO3$ as a Sensor for $CO_2$ Detection over a Wide Range of Concentration. Chemistry Letters 1711–1714, 1991.
12. Ishihara, T., Kometani, K., Hashida, M., Takita, Y.: Mixed Oxide Capacitor of $BaTiO_3$—PbO as a New Type $Co_2$ Gas Sensor. Chemistry Letters 1163–1166, 1990.
13. Isihara, T., Kometani, K., Mizuhara, Y., Takita, Y.: Capacitive Type Gas Sensor for the Selective Detection of Carbon Dioxide. Technical Digest of the Fourth International Meeting on Chemical Sensors, Tokyo 538–541, 1992.
14. Isihara, T., Kometani, K., Mizuhara, Y., Takita, Y.: Capacitive Type Gas Sensor for the Selective Detection of Carbon Dioxide. Sensors and Actuators B 13–14: 470–472, 1993.
15. Tränkler, H. -R.: Gassensorik heute und morgen. Sensor Report 1:32–39, 1993.
16. Hermans, E. C. M.: CO, $CO_2$, $CH_4$ and $H_2O$ Sensing by Polymer Covered Interdigitated Electrode Structures. Sensors and Actuators 5:181–186, 1984.

What is claimed is:

1. A semiconductive solid-state chemical sensor comprising a ceramic carrier having on one side a heating element with branch circuit connections and on the other side interdigitated electrodes and thereupon a gas sensitive material disposed as a thick film, wherein the gas sensitive material comprises CuO, Ba—$TiO_3$, and $Cu_xCe_yO_z$ in sintered form as a catalyst or adhesion compound, wherein x, y, and z are in the range of approximately 1–5, and x, y and z do not have to be integers.

2. A sensor according to claim 1, wherein the gas sensitive material is disposed at a thickness of approximately 20 to 200 μm.

3. A sensor according to claim 2, wherein $Cu_xCe_yO_z$ is present at approximately 0.1 to 10%.

4. A sensor according to claim 1, wherein the gas sensitive material has a grain size of less than approximately 5 μm.

5. A sensor according to claim 1, wherein $Cu_xCe_yO_z$ is present at approximately 0.1 to 10%.

6. A sensor according to claim 1, wherein said interdigitated electrodes comprise gold or another precious metal.

7. A sensor according to claim 1, wherein the heating element comprises platinum or palladium.

8. A method for detecting changes in $CO_2$ concentration, comprising:

contacting a gas with a sensor as claimed in claim 1; and measuring changes in the resistance of said sensor.

9. The method of claim 8, wherein said sensor has an operating temperature of 570° C.

10. A method for preparing a semiconductive solid-state sensor, comprising:

providing a solid substrate, attaching on one side of the substrate a heating element, attaching on another side of the substrate interdigitated electrodes, and operably disposing upon the electrodes a gas sensitive material comprising CuO, Ba—$TiO_3$, and $Cu_xCe_yO_z$ in sintered form as a catalyst or adhesion compound, wherein x, y, and z are in the range of approximately 1–5, and x, y and z do not have to be integers.

11. A semiconductive solid-state chemical sensor, comprising a ceramic carrier having a heating element with branch circuit connections on one side and interdigitated electrodes and a $CO_2$ gas sensitive material on the other side, wherein conductivity is measured by measuring resistance as the $CO_2$ concentration changes, wherein said $CO_2$ gas sensitive material comprises CuO, $BaTiO_3$, and $Cu_xCe_yO_z$, wherein x, y, and z are in the range of approximately 1–5, and x, y and z do not have to be integers, and wherein said $CO_2$ gas sensitive material is sintered and has a film thickness of approximately 20 to 200 μm.

12. A sensor according to claim 11, wherein said $CO_2$ gas sensitive material has grain sizes of less than 5 μm.

13. A sensor according to claim 12, wherein said grain size are in a range of 1–400 nm.

14. A sensor according to claim 11, wherein $Cu_xCe_yO_z$ is present in an amount of 0.1 to 10%.

15. A sensor according to claim 11, wherein the interdigitated electrodes comprise gold or another precious metal and the heating element comprises platinum or palladium.

* * * * *